United States Patent [19]
Petrofsky et al.

[11] Patent Number: 4,569,352
[45] Date of Patent: Feb. 11, 1986

[54] FEEDBACK CONTROL SYSTEM FOR WALKING

[75] Inventors: Jerrold S. Petrofsky, Beavercreek; Chandler A. Phillips, Tipp City; Harry H. Heaton, III, Beavercreek, all of Ohio

[73] Assignee: Wright State University, Dayton, Ohio

[21] Appl. No.: 671,805

[22] Filed: Nov. 15, 1984

Related U.S. Application Data

[63] Continuation of Ser. No. 494,219, May 13, 1983, abandoned.

[51] Int. Cl.$^4$ .............................................. A61N 1/36
[52] U.S. Cl. .............................................. 128/423 W
[58] Field of Search ................... 128/1 R, 421–423, 128/80 G; 3/1, 1.1, 1.2

[56] References Cited

U.S. PATENT DOCUMENTS

| | | | |
|---|---|---|---|
| 3,083,712 | 4/1963 | Keegan | 128/423 |
| 3,204,637 | 10/1965 | Frank et al. | 128/423 |
| 3,344,792 | 10/1967 | Offner et al. | 128/419 |
| 3,769,636 | 11/1973 | Friedman | 3/1.1 |
| 3,929,335 | 12/1975 | Malick | 272/57 |
| 4,030,141 | 6/1977 | Graupe | 3/1.1 |
| 4,147,171 | 4/1979 | Greene et al. | 128/421 |
| 4,165,750 | 8/1979 | Aleev et al. | 128/422 |
| 4,252,112 | 2/1981 | Joyce | 128/80 G |
| 4,499,900 | 2/1985 | Petrofsky et al. | 128/423 W |

OTHER PUBLICATIONS

Restoration of Hand Function in the Quadriplegic through Electrical Stimulation, Peckham et al., published in text entitled "Functional Electrical Stimulation", Marcell Dekker, Inc. 1979, pp. 83–95.

Microprocessor Controlled Stimulation in Paralyzed Muscle—Petrofsky et al., IEEE NAECON Record (1979) pp. 198–210.

Programmed Six-Channel Electrical Stimulator for Complex Stimulation of Leg Muscles During Walking—Strojnik et al.—IEEE Transactions on Biomedical Engineering, vol. BME-26, No. 2, Feb. 1979—pp. 112–116.

Closed-Loop Control of Force During Electrical Stimulation of Muscle—Crago et al.—IEEE Transactions on Biomedical Engineering, vol. BME-27, No. 6, Jun. 1980—pp. 306–312.

Walking Away from Paralysis—Discover Magazine—May 1981 pp. 26–29.

*Primary Examiner*—William E. Kamm
*Assistant Examiner*—Mitchell J. Shein
*Attorney, Agent, or Firm*—Biebel, French & Nauman

[57] ABSTRACT

A computer algorithm and hardware are disclosed for feedback control of movement in man for standing and walking. The system measures motion of the hips, knees and ankles and generates control signals for ten different muscle groups. Hip and knee supports are provided for restricting hip and knee movement to a common plane.

9 Claims, 10 Drawing Figures

FEEDBACK CONTROL SYSTEM FOR WALKING

This is a continuation of co-pending application Ser. No. 06/494,219 filed on 5/13/83 now abandoned.

BACKGROUND OF THE INVENTION

The present invention relates to a closed loop control system for enabling standing and walking by paraplegic or quadriplegic persons. So far as is known this has never been achieved prior to the completion and testing of the present invention. Typical prior art consists of powered exoskeletal apparatus of the general type disclosed in Mizen U.S. Pat. No. 3,449,769. Such prior art devices include a structure which is worn by a person and which includes sensor assemblies adapted to respond to normal movement of the wearer. Output signals from the sensor assemblies are amplified and used to drive servomotors which power the exoskeletal structure.

While the above described prior art enables a man to perform tasks otherwise beyond his physical ability, there has been no means for enabling walking through the use of muscles which are totally paralyzed. That objective is achieved by the present invention which grew out of early research as described in an article entitled "Walking Away from Paralysis" appearing in Discover magazine, May, 1981, page 26 et seq and in an article entitled "Microprocessor Controlled Stimulation in Paralyzed Muscle", IEEE NAECON Record (1979), pages 198 through 210. The achievement of such walking involves the use of devices for feedback controlled stimulation of paralyzed muscle, as generally taught in Petrofsky et al Ser. No. 417,934, Petrofsky et al Ser. No. 417,938 now U.S. Pat. No. 4,421,336, Petrofsky et al Ser. No. 417,935 now U.S. Pat. No. 4,480,830 and Petrofsky et al Ser. No. 444,647.

SUMMARY OF THE INVENTION

This invention achieves standing and walking by paralyzed muscles through use of a novel stimulation and feedback technique. A programmed microprocessor produces hip movement by generating control signals for stimulation transducers which stimulate the iliacus and hamstring muscles. Rising movement of the knees toward a knee lock position is produced by the microprocessor through generation of control signals for stimulation transducers which stimulate the quadriceps muscles; gravitational forces being used for production of knee movement in the opposite direction. Finally, the microprocessor produces ankle movement through generation of control signals for stimulation circuits which stimulate the gastrocnemius and tibialis muscle groups. As the hip, knee and ankle motion progresses, corresponding feedback signals are generated by sensors mounted on the body, and these feedback signals are applied to the microprocessor for closed loop control of the stimulation control signals. Movement restriction means are provided for limiting movement of the hips and knees to a common plane, thereby limiting the number of muscle groups requiring stimulation.

DESCRIPTION OF THE PREFERRED EMBODIMENTS

Figure 1:
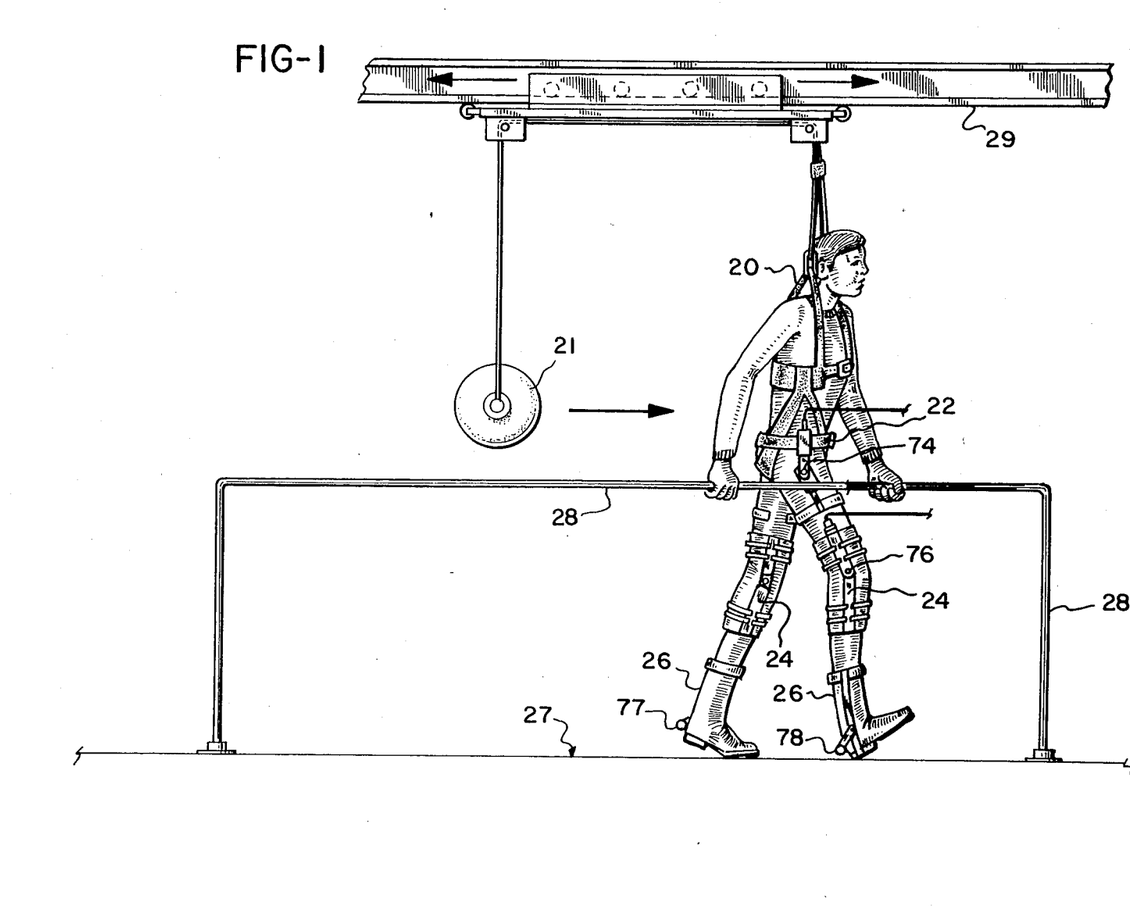
FIG. 1 is a schematic illustration of the placement of feedback sensors on the body of a paralyzed person who is walking in accordance with the teachings of this invention.

A feedback control system for controlling paralyzed muscles to produce walking may include a set of feedback sensors, mounted on the body as generally illustrated in FIG. 1. The sensor arrangement includes a pair of hip angle sensors 73, 74, a pair of knee angle sensors 75, 76 and a pair of ankle angle sensors 77, 78. (Sensors 73 and 75 not being visible in FIG. 1) A safety harness as generally illustrated at 20 protects the subject from loss of balance or computer malfunctions. This harness system consists of a sport parachute harness connected through nylon straps and webbing to a counter-balance system. The counter-balance system includes a weight 21 supported from the ceiling by a steel I beam 29 via a series of aircraft bearings. A forward weight (not illustrated) offsets inertia so that only a few ounces of force are required for moving the harness in the forward direction.

The counter-weight 21 partially offsets the weight of the body so that walking can be accomplished with only a fraction of the body weight. Such an arrangement is suitable for a paralyzed person who is just beginning to walk after years of inactivity. It has been found that suitable stability is obtained when the weight 21 supports approximately 70% of the body weight. An additional safety feature is provided by a pair of hand rails 28, 28 which are mounted in the floor 27.

Figure 2:
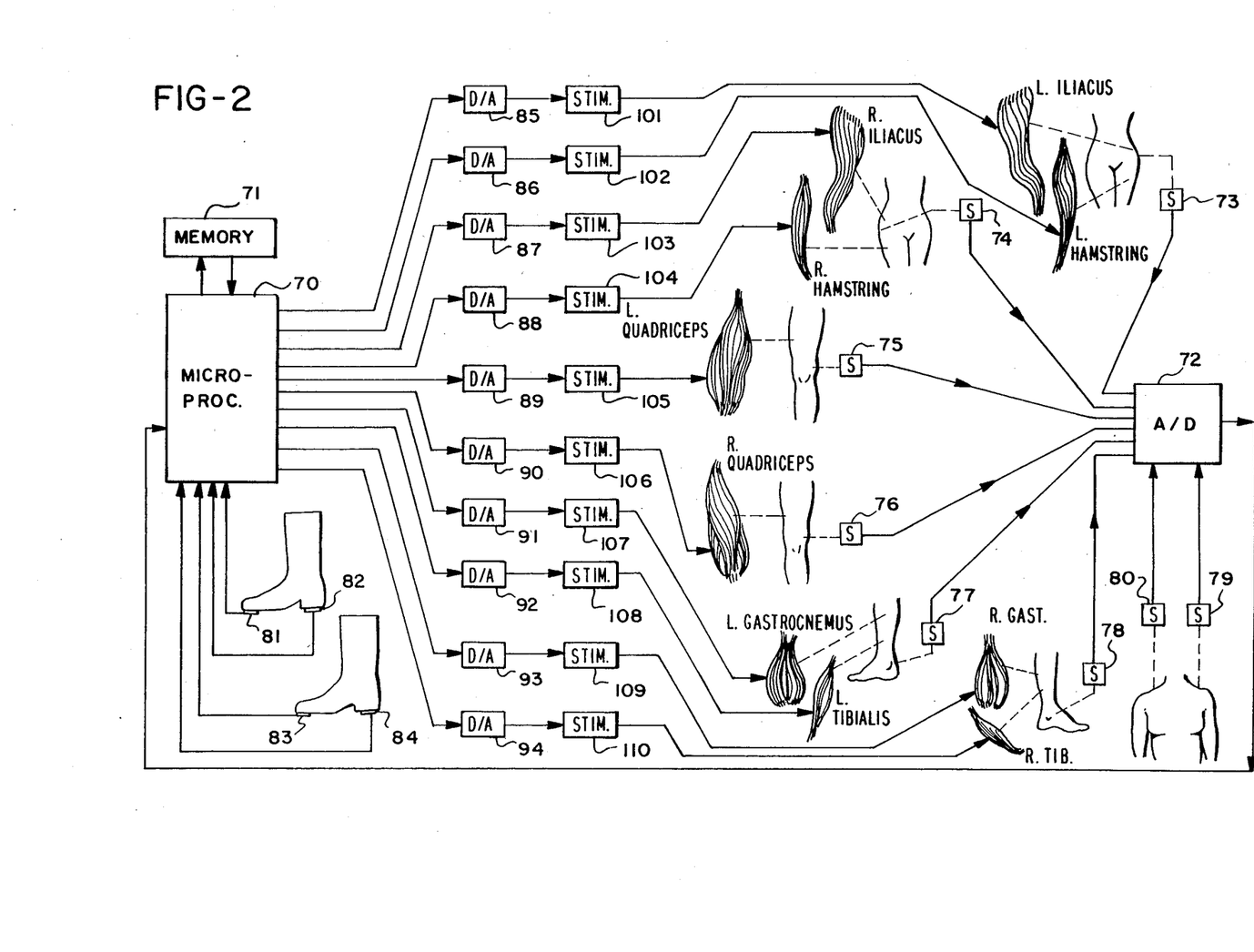
FIG. 2 is a block diagram of a feedback control system for walking.
Figure 3:
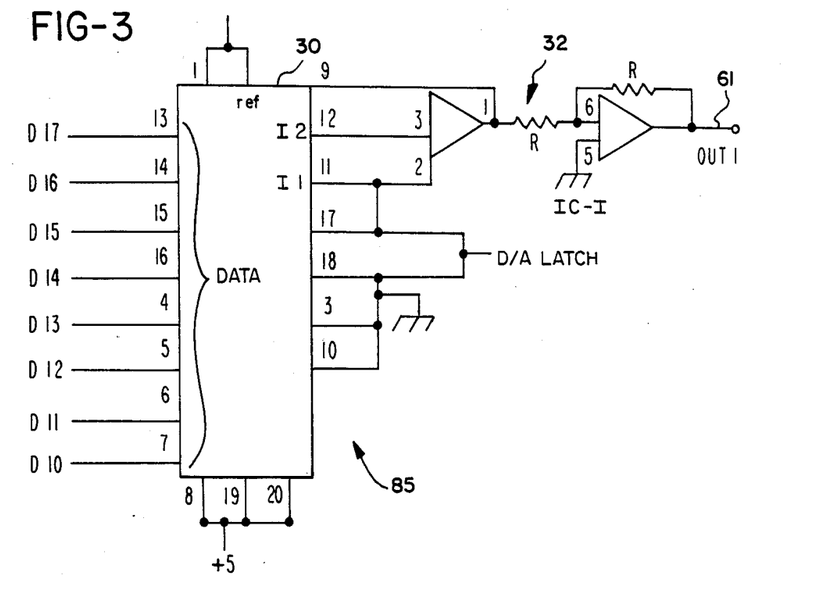
FIG. 3 is a schematic diagram of an interface circuit for interfacing a microprocessor to muscle stimulation circuitry.

The preferred embodiment of the invention, as generally illustrated in FIG. 2, includes a Z80 microprocessor 70 supported by 64K of dynamic memory 71. To interface the Z80 to the body ten sets of interface circuits 85 through 94 are utilized. These circuits may be constructed as generally illustrated in FIG. 3, and include a digital to analog converter 30, which preferably is a DAC0832 integrated circuit. Analog output signals from integrated circuits 30 are amplified by operational amplifier 32 (which preferably may be an LM1458 integrated circuits) for application to output terminal 61. The ten digital-to-analog converters may be addressed by using two 74LS138 integrated circuits (not illustrated). The 74LS138 integrated circuits decode simultaneous occurrence of I/D request and the appropriate eight addresses. The circuits are wired so that a high to low transition triggers acquisition of data off the microprocessor data bus. The amplified analog control signals, such as those appearing at terminal 61, are applied to ten stimulation circuits 101 through 110 as hereinafter described.

Feedback signals for controlling the microprocessor are produced by six sensors 73 through 78 mounted upon the body as above described in connection with FIG. 1. Output signals from the six sensors are applied to an eight channel analog-to-digital converter circuit 72 manufactured by Cromenco, Inc. The six feedback sensors are single turn precision potentiometers (10,000 OHMS) connected for sensing angular movements of the hips, knees and ankles of the subject. The sensors at the hip are worn on a hip support 22 comprising a waistband connected through a pair of metal rods to the upper legs. This allows single directional rotation of the hip in the front and back direction which is measured by rotational displacement of the potentiometers.

The system also includes a pair of custom knee supports 24, 24 which support the knees and prevent rotation in all but the forward and backward directions. Such rotational restriction coupled with the above mentioned restriction of hip movement results in movement of the hips and knees in a single plane. This simplifies the control equations by eliminating a number of muscles that normally are active with three-dimensional movement.

In order to support the ankles support boots 26, 26 are utilized. These boots are similar to standard U.S. Army military paratroop boots. The support from these boots is essential, because the ankle is one of the severest points of demineralization of bone (following spinal cord injury). Since paraplegic and quadriplegic subjects cannot feel their feet, it is necessary to modify the boots by installing zippers down the sides. This prevents undue stress across the ankle when putting the boots on or taking them off. Sensors 77, 78 measure the ankle angles by sensing the pivotal movement of metal strips attached to the outside surface of the boots.

In addition to the above mentioned ankle sensors the system utilizes toe sensors 81, 83 placed at the front of each boot and heel sensors 82, 84 placed at the back of each boot to indicate contact with the floor. These sensors are strictly off/on sensors, the output from which is provided to microprocessor 70 through a parallel port. The parallel port is a standard eight-bit digital parallel port commonly mounted with analog to digital converter 72. Finally, proportional sensors 79, 80 are placed on the shoulders of the subject. These sensors are used so that shoulder movement can be used to trigger the computer to initiate a walking sequence or a standing up sequence. The outputs from the shoulder sensors are also interfaced to the microprocessor through analog to digital converter 72.

Due to the restriction of movement of the hip, knee and ankle joints, only a relatively few muscles need to be controlled for producing standing or walking movement. Since the knee itself is a locking type of joint, only the quadriceps muscles are stimulated to move the knee to the locked position. Gravity is used to allow the knee to go to the unlocked position. To move the ankle backward, the gastrocnemius group muscles and the tibialis group muscles are stimulated. To move the hip back and forth the iliacus and hamstring groups are stimulated. Thus the system stimulates five muscle groups per leg or a total of ten muscle groups to control movement.

Each set of muscles is stimulated by sequential stimulation through three electrodes as is fully described in Ser. No. 417,934. Circuitry for generating stimulation signals for one set of electrodes 71, 72, 73 is illustrated generally in FIGS. 4 and 5. This circuitry is repeated for each of the blocks 101 through 110 of FIG. 2. In general, electrodes 71, 72 and 73 are placed on the surface of the skin at equal distances such that the center electrode is over the belly of the muscle (as its innervation point) and the other two electrodes are placed diagonally across the muscle. This allows approximately one-half of the muscle to be activated by each pair of electrodes when firing sequentially.

Figure 4:
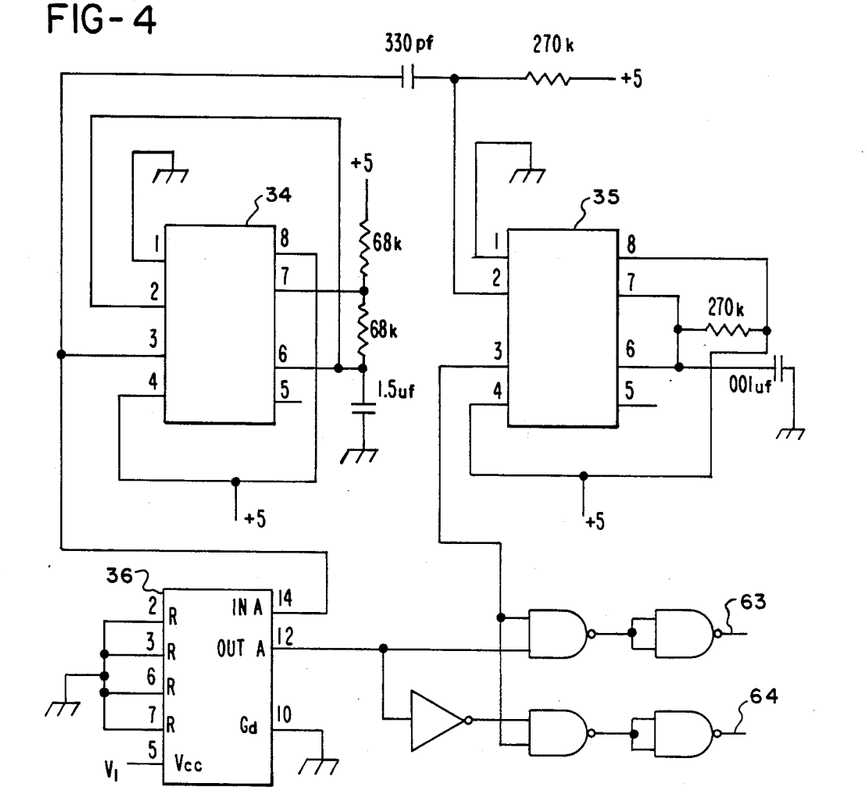
FIG. 4 is a schematic diagram of a circuit for generating pulsed stimulation control signals.
Figure 5:
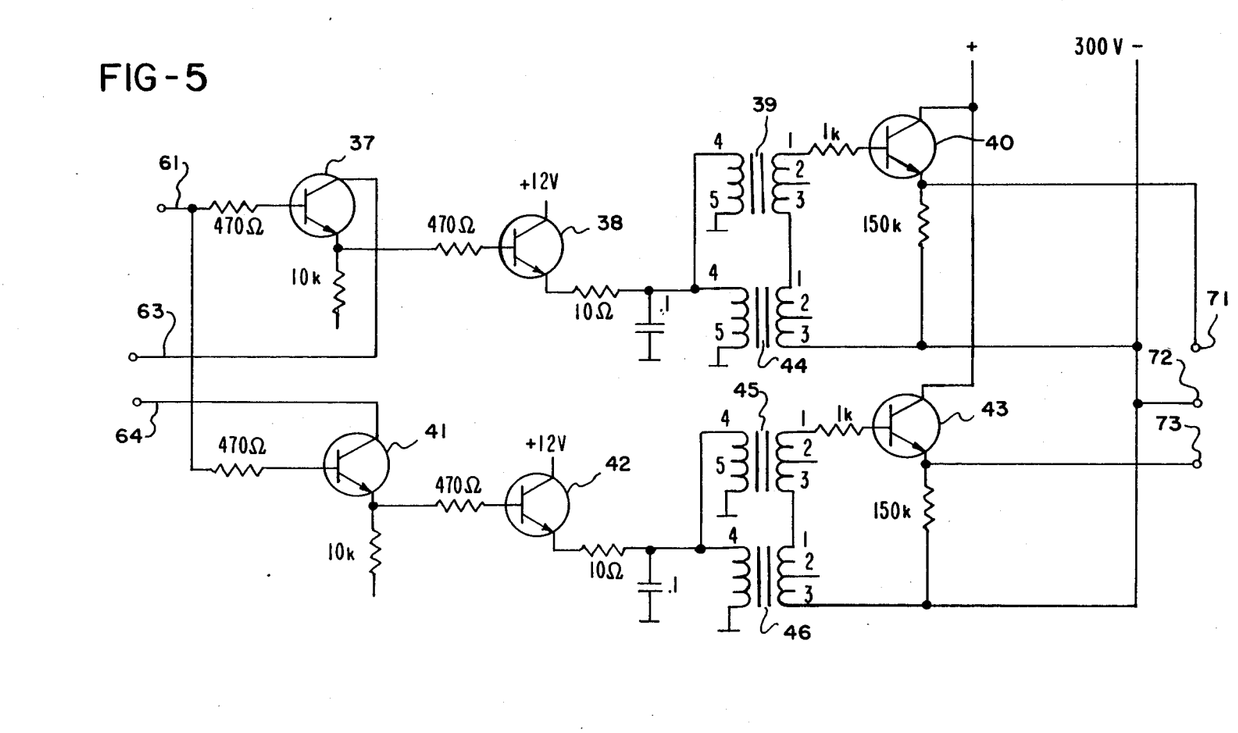
FIG. 5 is a schematic diagram of circuitry for stimulating a muscle.

The stimulation circuitry includes two NE555 integrated circuit timers 34 and 35 and a counter 36 (integrated circuit type SN7490), as illustrated in FIG. 4. This circuit creates a series of alternating pulses at output lines 63 and 64. Each signal is pulsed at a frequency of 50 Hz. These pulsed signals are applied to transistors 37 and 41, as generally illustrated in FIG. 5. Transistors 37 and 41, which may be type 2N3904 transistors, receive a base drive from line 61, which is the output from the interface circuit of FIG. 3. The circuitry of FIG. 5 amplifies the pulses appearing at input line 63 and 64 in accordance with the magnitude of the signal on line 61. Amplification is accomplished by transistors 38 and 42 (2N5295 devices) transformers 39, 44, 45, and 46, and transistors 40 and 43 (C1308K devices). The net result is a pair of amplitude modulated and alternatingly pulsed output signals across electrode terminal pairs 71/72 and 73/72.

Transistors 37 and 41 operate as current amplifiers and produce output pulses whose amplitude varies from 0 to 5 volts. This output is buffered through transistors 38 and 42 and inverted to high voltage by the illustrated transformer arrangement. The output from the transformers are amplified by transistors 40 and 43, which in turn is driven by a 300 volt isolated power supply. The output signals from transistors 40 and 43 are current limited through 1K resistors to prevent electrode burns.

Figure 6:
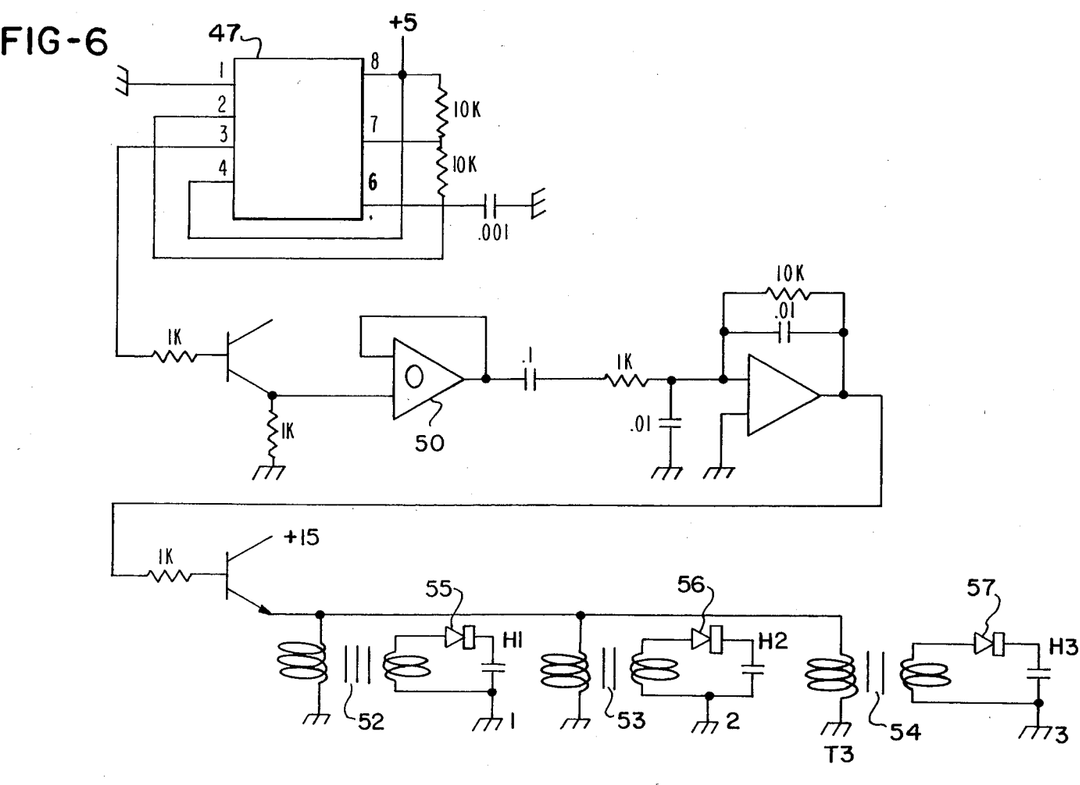
FIG. 6 is a schematic diagram of circuitry for generating isolated 300 volt driving signals.

The power supply, as illustrated in FIG. 6, is constructed by exciting inverted transformers 52, 53 and 54 by a 1,000 Hz signal provided from a free-running NE555 timer 47. This output is rectified by rectifiers 55, 56 and 57 to provide the required 300 volt source voltage.

As stated above, the stimulation control signals are amplitude modulated, and the modulating control signal is supplied by microprocessor 70. The software for controlling the microprocessor comprises three general sections. The first of these is "Stand-Up", the next one is "Stance" and the third is "Walking". Walking is a modification in software of the Stance routines.

Figure 7:
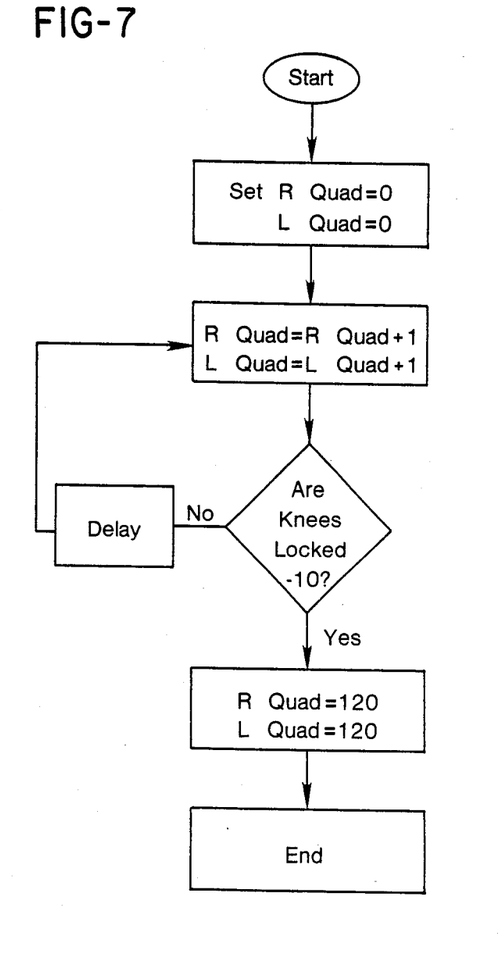
FIG. 7 is a flow chart for a "Stand-Up" computer sub-routine.

The Stand-Up routines are written as generally illustrated by the flow chart of FIG. 7. The muscles controlled to the largest extent in this routine are the quadriceps muscles. To stand up, the body weight is shifted forward and the quadriceps muscles are activated until the knees are extended in a locked position. The algorithm involves initially starting the quadriceps voltage in both muscles at zero and then slowly increasing the voltage in a ramp while checking to see if the knees are locked. If the knees are within 5° of being locked, this is sensed by the program and the quadriceps voltage is reduced to 120 units. The maximum output is 255 units, which corresponds to complete saturation of an eight-bit register. An output signal of 120 units corresponds to a signal ranging from 30 to 35 volts measured at the stimulation electrodes.

When the Stand-Up routine is executed there is rapid increase in stimulation voltage causing the muscles to contract at the knee (i.e. contraction of the quadriceps)

followed by a reduction in muscle stimulation once the knee is locked. The above mentioned output signal of 120 units is sufficient to generate approximately 10% of the strength of the quadriceps muscles. For most subjects this results in knee lock.

Figure 8:
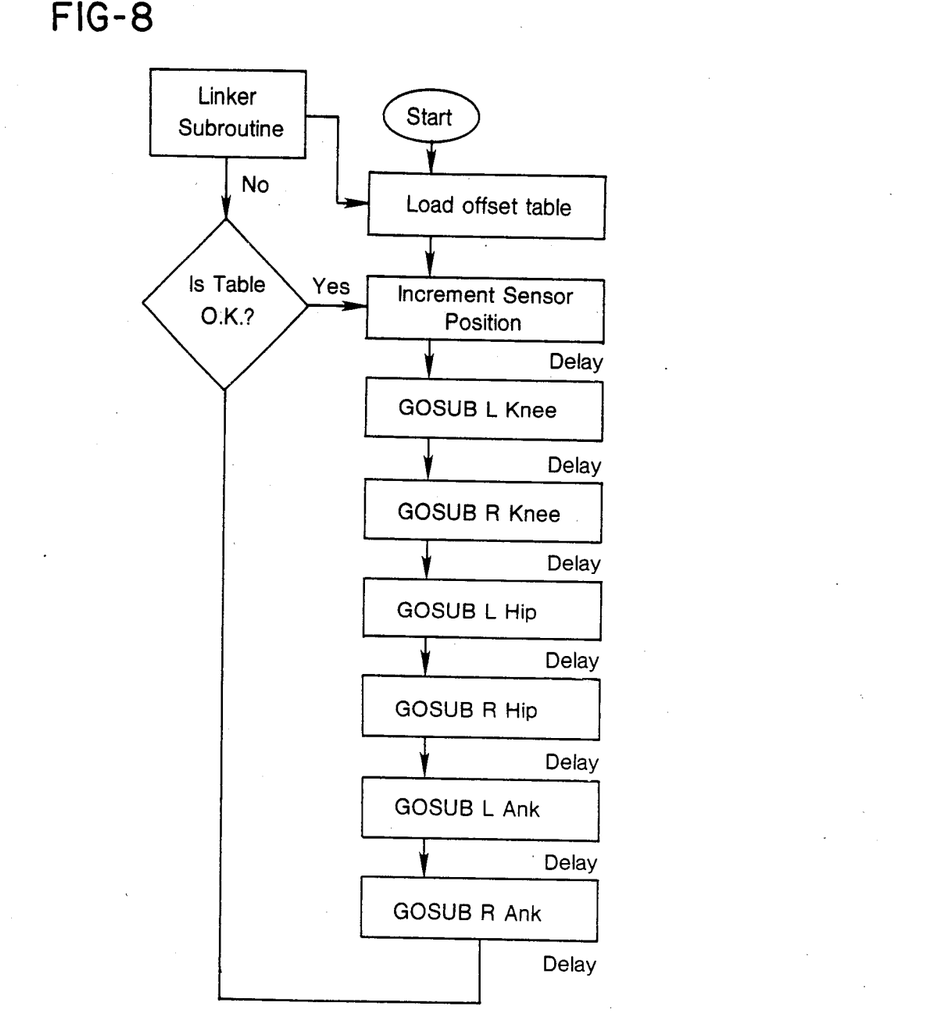
FIG. 8 is a flow chart for a "Stance" computer sub-routine.

After the Stand-Up routine has been completed, the computer switches to the Stance program which checks for knee lock and adjusts stimulation voltages appropriately to maintain that knee lock. The Stance program includes sub-routines as generally shown in FIG. 8. During this sub-routine the program automatically scans all six feedback sensors for verification of a proper standing position. The output signals from the sensors are buffered through a series of operational amplifiers with balance controls such that each sensor reads zero volts when the knees and ankles are in a locked position with the right leg backwards. This is the basic starting point for the Stance sub-routines.

Assuming all sensors read zero volts, entry into the Stance program is initiated by loading an offset table into the computer. The offset table is a table of values which allow the sensors to vary under software control (using the sub-routine labelled "Increment Sensor Position") by an offset so that the zero point (i.e. the point where the joint is assumed to be in the proper position) can vary from the locked position at the joint to either side of the locked position by adding or subtracting an offset from the sensor position. The offset table for standing is simply a series of zeros since no offset is required for that particular activity. When the offset table is added to the sensor positions with the knees in the locked position the output is all zeros.

Figure 9:
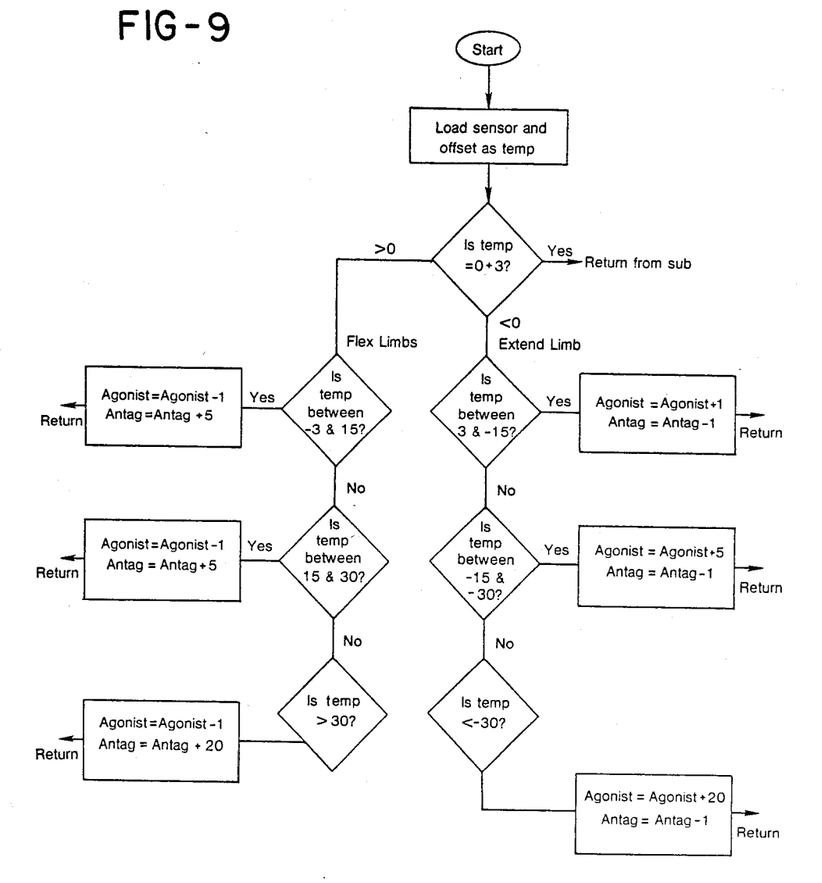
FIG. 9 is a flow chart for a "Joint" computer sub-routine.

After the sensor incrementing sub-routine (and in between all succeeding sub-routines) is completed, a small delay is initiated. This delays a timing loop to slow the sub-routines down or speed the sub-routines up respectively. The program then executes the left knee, right knee, left hip, right hip, left ankle and right ankle sub-routines. All of these sub-routines have essentially the same format. As shown in FIG. 9, a typical joint sub-routine program involves simply looking at the current sensor position and the sensor offset and determining if the sensor is in the zero position. If the sensor with offset is not equal to zero, further action of the sub-routine is required. Otherwise there is a return from the joint sub-routine to the routine of FIG. 8.

Using the knee as an example, a number of less than zero at this point in the program indicates that the knee is flexed too far and needs to be extended. This is accomplished by stimulating the agonist muscles associated with extending the knee and cutting the activity of the antagonist. Action of the antagonist muscles is set up through a successive windowing technique. For example, if the position of the sensor is close to that required, voltages are increased and decreased by only a single unit. If the sensor is somewhat farther off, voltages are increased or decreased substantially, and, if the sensor position is very far off from where it should be, then there is a large change in voltage. In this manner, voltage is supplied in almost a logarithmic function to rapidly bring the muscle back to the proper level appropriate for that target.

Figure 10:
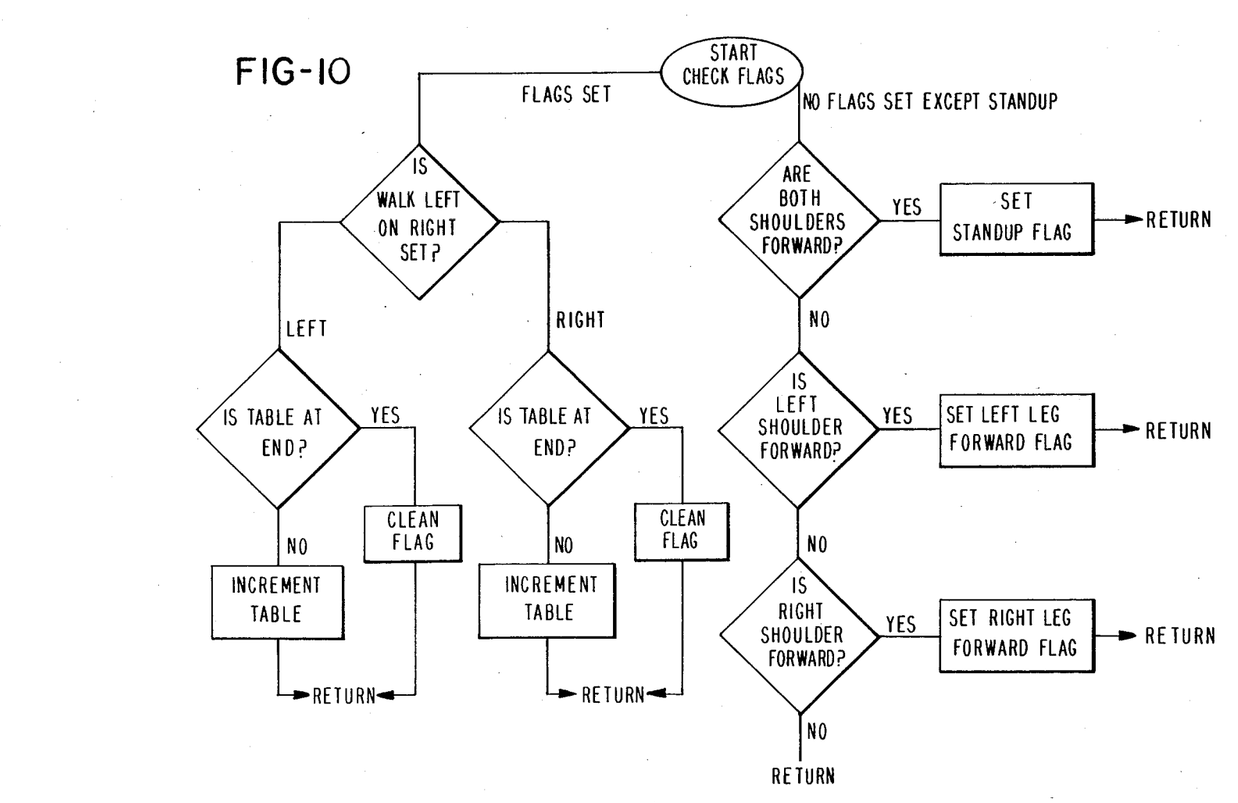
FIG. 10 is a flow chart for a "Linker" computer sub-routine.

After all six sub-routines have been completed, the program enters the Linker sub-routine, as illustrated in FIG. 10. The purpose of the Linker sub-routine is to determine if the subject desires to continue to stand or to move. The Linker sub-routine is set under software control to look for a shoulder movement of the right or left shoulder indicating the subject's desire to extend the right or left leg forward. It is possible to extend this concept by adjusting the size of the step as a function of the degree of extension of the shoulder. As illustrated herein, the Linker sub-routines merely set flags in the computer if one shoulder or the other is set forward. When flags are set in response to a shoulder movement, the program begins the walking sequence.

During the Walking sequence, the Stance sub-routines continue to be used. However, walking is put into place by triggering a sequence of activation of rapid changes in the offset table added to the initial sensor positions. For example, Stance is accomplished by setting all sensors to zero. The computer then does a seek and search at the joints to keep all the joints locked with the sensors in this position. This is used to initiate walking.

Walking is divided into four phases. Each phase is adjusted by rapidly changing the table for the sensor positions and scanning through the stance table. The first activity is to raise the right heel. This is accomplished by offsetting the hip, knee and ankle sensor positions for both legs through a rapidly changing offset table until the right heel is lifted off the floor. This terminates the first phase of walking. The next phase of walking involves lifting the hip. Again, by rapidly changing the position of the sensors, the leg is forced to move through a controlled sequence at a controlled rate by adjusting the delays in the Stance sub-routine. This is accomplished until the right toe leaves the floor. Once the right toe has left the floor, the next stance of walking involves straightening out the right leg.

Once the knee has been extended and locked, the final sub-routine involves pushing the body forward to go to a position standing with the right leg forward and the left leg back. This is accomplished by contracting the appropriate gastrocnemius muscle to move the opposite ankle. This automatic sequence moves the body to the final position by rapidly processing sub-routines incrementing the position of the legs.

It should be appreciated that the invention as herein described may be modified in a number of ways. For instance, the stimulation control electrodes may be implanted within the body either above the muscles being controlled or near the respective motor nerves. Balance in walking may be improved by use of an appropriate level sensing arrangement.

It has been found that while spinal cord damage prevents voluntary movement of the leg muscles a person who is so injured may still be able to generate electrical nerve signals indicating an intention to move the paralyzed muscles. These nerve signals may be picked up by sensors placed on the body and utilized to produce voluntary closed loop walking control in accordance with the practice of this invention.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. A feedback control system for walking comprising:
means for restricting the hips and knees to common plane movement,
first stimulation means for stimulating the iliacus and hamstring muscle groups to produce hip movement in said common plane, first sensing means for sensing hip movement and generating a first feedback signal in correspondence therewith, second stimulating means for stimulating the quadriceps muscle groups to produce knee movement in said common plane in coordination with said hip movement, second sensing means for sensing said knee movement and generating a second feedback signal in correspondence therewith, means for supporting the ankles, third stimulation means for stimulating the gastrocnemius and tibialis muscle groups to produce ankle movement which is coordinated with said hip and knee movement, third sensing means for sensing said ankle movement and generating a third feedback signal in correspondence therewith, and programmed microprocessor means for receiving said first, second and third feedback signals and generating control signals for said first, second and third stimulating means.

2. A feedback control system according to claim 1 and further comprising fourth sensing means for sensing shoulder movement and generating a fourth feedback signal in correspondence therewith;

said microprocessor being connected for reception of said fourth feedback signal and programmed for timing the generation of said control signals in response to said fourth feedback signal.

3. A feedback control system according to claim 2 and further comprising foot sensors for sensing contact of the heels and toes with the floor and signaling said contact to said microprocessor.

4. Apparatus for stimulation of human walking comprising:

stimulation means for electrically stimulating muscles in both legs of said human to produce coordinated movement of said legs, means for restricting the hips and knees of said human to common plane movement, support means for the ankles of said human leg sensing means for sensing the positions of said legs and generating leg position signals corresponding thereto, sensing means for sensing a voluntary movement of said human and generating sequence initiation signals corresponding thereto, and computing means responsive to said leg position signals and said sequence initiation signals for controlling said stimulation means.

5. Apparatus according to claim 4 wherein said means for sensing voluntary movement comprises means for sensing movement of the shoulders of said human.

6. A feedback control system for walking comprising:

means for restricting the hips and knees to common plane movement, means for supporting the ankles during said hip and knee movement first stimulation means for stimulating hip movement in said common plane, first sensing means for sensing hip movement and generating a first feedback signal in correspondence therewith, second stimulating means for stimulating knee movement in said common plane in coordination with said hip movement, second sensing means for sensing said knee movement and generating a second feedback signal in correspondence therewith, third stimulation means for stimulating ankle movement which is coordinated with said hip and knee movement, third sensing means for sensing said ankle movement and generating a third feedback signal in correspondence therewith, and programmed microprocessor means for receiving said first, second and third feedback signals and generating control signals for said first, second and third stimulating means.

7. A feedback control system according to claim 6 and further comprising fourth sensing means for sensing shoulder movement and generating a fourth feedback signal in correspondence therewith;

said microprocessor being connected for reception of said fourth feedback signal and programmed for timing the generation of said control signals in response to said fourth feedback signal.

8. A feedback control system according to claim 7 and further comprising foot sensors for sensing contact of the heels and toes with the floor and signaling said contact to said microprocessor.

9. Apparatus for stimulated walking comprising:

stimulation means for electrically stimulating the muscles of both legs of a human being to produce coordinated walking movement, sensing means for sensing the positions of said legs and generating feedback signals corresponding thereto, computing means responsive to said feedback signals for controlling said stimulation means, and overhead support means comprising:
  a harness for attaching to the body of said human being,
  a counterweight attached to said harness for counterbalancing the weight of said human being, and
  an overhead support member for supporting said counterweight and a portion of the weight of said human being.

* * * * *